(12) United States Patent
Tanida et al.

(10) Patent No.: US 6,829,918 B2
(45) Date of Patent: Dec. 14, 2004

(54) METHOD OF AND APPARATUS FOR MEASURING MERCURY CONTAINED IN HYDROCARBON

(75) Inventors: Koji Tanida, Takatsuki (JP); Atsushi Endo, Takatsuki (JP); Munehiro Hoshino, Takatsuki (JP)

(73) Assignee: Nippon Instruments Corporation, Osaka (JP)

( * ) Notice: Subject to any disclaimer, the term of this patent is extended or adjusted under 35 U.S.C. 154(b) by 0 days.

(21) Appl. No.: 10/219,662

(22) Filed: Aug. 16, 2002

(65) Prior Publication Data

US 2004/0031313 A1 Feb. 19, 2004

(51) Int. Cl.[7] .................... G01N 30/02; G01N 30/90
(52) U.S. Cl. .................... 73/23.39; 73/23.35; 73/23.2
(58) Field of Search ................ 73/23.39, 23.35, 73/23.2, 863.12; 436/76; 210/679, 288

(56) References Cited

U.S. PATENT DOCUMENTS

| | | | | |
|---|---|---|---|---|
| 3,194,629 A | * | 7/1965 | Dreibelbis et al. | 423/210 |
| 3,933,431 A | * | 1/1976 | Trujillo et al. | 436/76 |
| 4,080,169 A | * | 3/1978 | Kloosterboer et al. | 436/76 |
| 4,986,898 A | * | 1/1991 | Torihata et al. | 208/251 R |
| 5,082,569 A | * | 1/1992 | Homeier et al. | 210/679 |
| 5,510,565 A | * | 4/1996 | Tan et al. | 585/823 |
| 5,736,053 A | * | 4/1998 | Ikushima et al. | 210/688 |
| 6,129,843 A | * | 10/2000 | Petty et al. | 210/321.78 |
| 6,134,943 A | * | 10/2000 | Nakagawa et al. | 73/23.35 |
| 6,520,033 B1 | * | 2/2003 | Schroeder et al. | 73/863.12 |
| 2001/0034065 A1 | * | 10/2001 | Tyson et al. | 436/81 |

FOREIGN PATENT DOCUMENTS

EP 433677 A1 * 6/1991 .......... C10G/25/00

* cited by examiner

*Primary Examiner*—Hezron Williams
*Assistant Examiner*—Rodney T. Frank
(74) *Attorney, Agent, or Firm*—Birch, Stewart, Kolasch & Birch, LLP

(57) ABSTRACT

A method of and an apparatus for measuring mercury present in a hydrocarbon, wherein a gas (G) such as an air containing no mercury is allowed to flow through a column filled with an adsorbent material effective to adsorb mercury, and a hydrocarbon sample to be measured is injected into the column to allow the mercury contained therein to be adsorbed by the adsorbent material while removing a volatile component other than mercury therefrom, and measuring the amount of mercury using mercury measuring instrument.

10 Claims, 1 Drawing Sheet

METHOD OF AND APPARATUS FOR MEASURING MERCURY CONTAINED IN HYDROCARBON

BACKGROUND OF THE INVENTION

1. Field of the Invention

The present invention relates to a method of and apparatus for measuring mercury contained in a hydrocarbon such as, for example, naphtha and LPG (liquefied petroleum gas).

2. Description of the Prior Art

It has been well known in the art that hydrocarbons such as, for example, naphtha, contain mercury, particularly dimethylmercury. It is also well known that various components of mercury are responsible for the degradation of the capacity of a catalyst such as paradigm or platinum employed for producing various kinds of petrochemical products from naphtha. For this reason, countermeasures have been considered necessary to measure the amount of mercury contained in hydrocarbon and to remove the mercury when the amount of mercury contained in the hydrocarbon exceeds a predetermined value.

Hitherto, attempts for mercury measurement have been made to use a heated vapor analyzing device including a sample port in which a sample comprising hydrocarbon is directly injected. With this heated vapor analyzing device, mercury contained in the sample is measured after having been vaporized by heating the sample port within a combustion tube. Also, during the measurement, additives are added together with the sample to remove interfering gases that are generated from the sample and are likely to disturb the mercury measurement.

However, with the conventional method of measuring mercury discussed above, it has been experienced that when mercury contained in the sample is vaporized by heating, hydrocarbon is simultaneously volatized from the sample to produce an inflammable gas. Accordingly, in order to avoid a rapid generation of the inflammable gas, stringent measurement conditions are required as to the quantity, type and flow rate of the sample and also as to the temperature rise rate of the sample and so on. Also, similarly stringent requirements are imposed on selection of the additives.

SUMMARY OF THE INVENTION

In view of the foregoing, the present invention is intended to provide a method of and an apparatus for measuring mercury, which are effective to measure mercury easily with the above discussed stringent measurement conditions being alleviated.

In order to accomplish the foregoing object of the present invention, there is, in accordance with one aspect of the present invention, provided a method of measuring mercury that is carried out by causing a mercury-free gas, i.e., a gas containing no mercury, to flow through a column filled with an adsorbent material effective to adsorb mercury. While the mercury-free gas flows through the adsorbent containing column, the hydrocarbon to be measured is injected to allow mercury, contained in the hydrocarbon, to be adsorbed by the adsorbent material to thereby remove a volatile component other than mercury, followed by measurement of the mercury with the use of a mercury measuring instrument.

In the practice of the foregoing embodiment of the mercury measuring method of the present invention, while the mercury-free gas flows through the column, hydrocarbon to be measured is injected into the column and mercury contained in the hydrocarbon is then adsorbed by the adsorbent material within the column. The hydrocarbon from which the mercury is thus removed is subsequently discharged to the outside together with the gas and is removed out of the column. The column is thereafter inserted in the mercury measuring instrument so that the mercury adsorbed by the adsorbent material within the column is heated to vaporize and is then measured.

During the measurement, even though the mercury is heated to vaporize, no inflammable gas is generated since the hydrocarbon has already been removed from the column. Also, since only the carrier air containing no mercury, that is, the mercury-free carrier air which flows through the column, and mercury adsorbed by the adsorbent material are present within the column and no interfering gas such as hydrocarbon which would otherwise interfere with measurement of the mercury is present within the column, the present invention is effective to dispense with the use of any additives hitherto required to remove the interfering gas. Because of this, the present invention makes it possible to perform the mercury measurement easily without requiring such stringent measurement conditions as hitherto required. Yet, in contrast to the prior art in which for the purpose of securing a safety the maximum amount of hydrocarbon that can be measured at a time is limited to 100 $\mu$L, the present invention allows an increased amount of hydrocarbon, say, 200 $\mu$L or more, to be measured at a time and, therefore, the mercury contained in the hydrocarbon can be accurately measured.

In a different embodiment of the mercury measuring method of the present invention, a feature thereof resides in that organic mercury and metallic mercury contained in hydrocarbon are measured by differentiatedly collecting them. More specifically, the present invention also provides a method of measuring organic mercury and metallic mercury contained in hydrocarbon by differentiatedly collecting the organic mercury and the metallic mercury, which is carried out by preparing first column, filled with a first absorbent material effective to adsorb organic mercury, and a second column fluid-connected in series with the first column and filled with a second adsorbent material effective to adsorb metallic mercury; injecting hydrocarbon to be measured into the first column while a gas containing no mercury is allowed to flow through the first and second columns sequentially; heating the first column to transform the metallic mercury contained in the hydrocarbon into a gaseous fluid so as to flow through the first adsorbent material and also as to cause the organic mercury to be adsorbed by the first adsorbent material; causing the second adsorbent material within the second column to adsorb the metallic mercury; and measuring the organic mercury and the metallic mercury, which have been differentiatedly collected by the first and second columns, respectively, by means of a mercury measuring instrument.

In the practice of the mercury measuring method according to the different embodiment of the present invention, while the mercury-free gas flows through the first and second columns, hydrocarbon to be measured is injected into the first column. Since the first column is heated, metallic mercury contained in the hydrocarbon is gasified and flows through the first adsorbent material within the first column, while only organic mercury contained therein is allowed to be adsorbed by the first adsorbent material. The gasified metallic mercury is fed to the second column together with the mercury-free gas and the gaseous metallic mercury is subsequently adsorbed by the second adsorbent material within the second column. The hydrocarbon from which the organic and metallic mercury is thus removed is subsequently discharged to the outside together with the gas and is removed out of the first and second columns. The first and second columns are thereafter inserted in the mercury measuring instrument so that the organic and metallic mercury adsorbed differentiatedly collected by the first and second adsorbent materials within the first and second columns, respectively, are heated to vaporize and are then measured.

At this time, as is the case with the mercury measuring method according to the previously described embodiment of the present invention, even though the organic and metallic mercury is heated to vaporize, no inflammable gas is generated since the hydrocarbon has already been removed from the first and second columns. Also, since no interfering gas which would otherwise interfere with measurement of the mercury is present within the first and second columns, the present invention is effective to dispense with the use of any additives hitherto required to remove the interfering gas. Because of this, the present invention makes it possible to perform the mercury measurement easily without requiring such stringent measurement conditions as hitherto required.

In the practice of any of the foregoing mercury measuring methods, the mercury-free gas may be air.

In another aspect of the present invention, there is provided a mercury measuring apparatus designed to perform the first mentioned embodiment of the mercury measuring method. This mercury measuring apparatus includes a column filled with an adsorbent material effective to adsorb mercury in hydrocarbon; a pump for flowing through the column a gas containing no mercury; an injector for injecting hydrocarbon to be measured into the column while the gas flows through the column; and a mercury measuring instrument for measuring mercury which has been adsorbed by the adsorbent material.

There is also provided a mercury measuring apparatus designed to perform the second mentioned embodiment of the mercury measuring method. This mercury measuring apparatus includes a first column, filled with a first adsorbent material effective to adsorb organic mercury; a heater for heating the first column so as to allow a gaseous metallic mercury, contained in the hydrocarbon, to flow through the first adsorbent material; a second column connected in series with the first column and filled with a second adsorbent material effective to adsorb metallic mercury; a pump for flowing a gas, containing no mercury, through the first and second columns sequentially; an injector for injecting the hydrocarbon to be measured into the first column while the gas containing no mercury flows therethrough; and a mercury measuring instrument for measuring the organic mercury and the metallic mercury which have been differentiatedly collected by the first and second columns, respectively.

The injector referred to above may be a micro-syringe. Also, the gas containing no mercury may be air, in which case the pump is disposed downstream of the column with respect to a direction of flow and a mercury removal filter is preferably disposed upstream of the column for removing mercury from air to achieve a mercury-free flow through the column.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Figure 1:
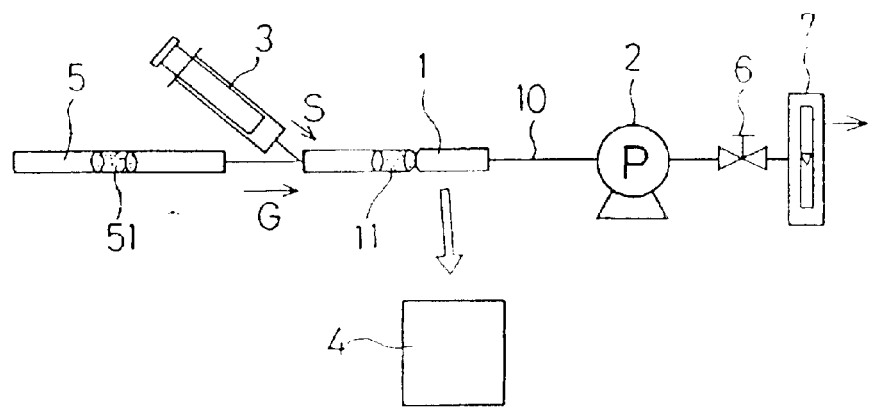
FIG. 1 illustrates a fluid circuit employed in a mercury measuring apparatus according to a first preferred embodiment of the present invention.

FIG. 1 shows a schematic configuration of a mercury measuring apparatus according to a first preferred embodiment of the present invention, which includes a generally elongated tubular column 1 having its opposite ends fixed with silica wool and also having its interior filled with a mass of adsorbent material 11, a suction pump 2 disposed downstream of column 1 with respect to the direction of flow of a carrier gas G towards a flow meter 7 and operable to feed the carrier gas G, an injector 3, for example, a micro-syringe for injecting a sample S containing hydrocarbon into the column 1 while the gas G is flowing through the column 1, and a mercury measuring instrument 4 for thermally vaporizing and measuring the mercury (such as organic mercury and metallic mercury) that has been adsorbed by the adsorbent material 11 within the column 1. The carrier gas G referred to above contains no mercury (neither organic mercury nor metallic mercury) and may be air. The mercury measuring instrument 4 referred to above may be a heated vapor analyzing device such as, for example, an atomic absorption mercury photometer.

The adsorbent material 11 disposed in column 1 is preferably employed in the form of a material capable of exhibiting excellent adsorbability with respect to metallic mercury and organic mercury (a mercury compound such as dimethylmercury) that is contained in a hydrocarbon material such as naphtha. Both metallic mercury and organic mercury are harmful substances produced during the manufacture of petroleum chemicals. Absorbent materials include activated alumina ($Al_2O_3$), which is effective in forming an amalgam such as gold or silver, or absorbent materials prepared by coating the carrier particulates with a material which is effective in forming said amalgam. In particular, the activated alumina referred to above has an excellent capacity for adsorbing organic mercury whereas the latter two materials have an excellent capacity for adsorbing metallic mercury. For the injector 3, a micro-syringe is suitably employed since the sample S can advantageously be injected into the column 1 in a short length of time and in one stroke.

In the embodiment shown in FIG. 1, a mercury removal filter 5 filled with a filler material 51 and effective to remove mercury contained in the air G is positioned upstream of and in fluid communication with the column 1. Since this mercury removal filter 5 is operable to remove mercury contained in the air G, the use of the mercury removal filter 5 is effective in avoiding an ingress of mercury, contained in the gas G, into the column 1 and, hence, to avoid any possible error which would otherwise occur in the measurement of mercury contained in the sample S. The filler material 51 within the mercury removal filter 5 is preferably employed in the form of a mass of particulates or fine woolen fibers of gold or silver of a kind capable of forming an amalgam as the reaction product with mercury contained in the gas G. A mass of porous carrier particulates having their surfaces coated with gold or silver can also be used. Positioned between a downstream side of the suction pump 2 and the flow meter 7 is a control valve 6. Thus, from the upstream side to the downstream side of the system, the mercury removal filter 5, the column 1, the suction pump 2, the control valve 6 and the flow meter 7 are connected in series with each other by means of a tubing 10 in the order specified above.

A method of measuring the mercury according to the first embodiment of the present invention will now be described.

Assuming that the suction pump 2 is being driven, the carrier gas, that is, the air G is sucked by the suction pump 2 and is fed towards the column 1 through the mercury removal filter 5 at the rate of about 0.2 L/min. The air G contains mercury and this mercury is removed by adsorption by the filter material 51 in the mercury removal filter 5 as the air G flow through the mercury removal filter 5. The air G from which the mercury has been removed is subsequently supplied towards the column 1.

While the air G flows through the column 1 in the manner described above, the sample S containing hydrocarbon such as naphtha to be measured is injected into the interior of the column 1. As the injected sample S flows through the adsorbent material 11 in the column 1 together with the mercury-free air G, organic mercury and metallic mercury both contained in the sample S are adsorbed and collected by the adsorbent material 11. The sample S from which the mercury has been so removed, that is, the mercury-free sample S is subsequently drawn outwardly by the suction pump 2 together with the mercury-free air G and is thus removed out of the column 1. Thereafter, the column 1 is removed from the tubing 10 and is then placed in the mercury measuring instrument 4 such as a heated vapor analyzing device so that the total mercury can be measured by heating and, hence, vaporizing the mercury that has been adsorbed and collected by the adsorbent material 11 within the column 1.

In this mercury measuring instrument 4, when the mercury adsorbed by the adsorbent material 11 is vaporized by heating, no inflammable gas will be generated since the hydrocarbon contained in the sample S has already been removed from the column 1. Also, since only the carrier air G containing no mercury, that is, the mercury-free carrier air G and the mercury adsorbed by the adsorbent material 11 are present within the column 1 and no interfering gas such as hydrocarbon which would otherwise interfere with measurement of the mercury is present within the column 1, the present invention is effective to dispense with the use of any additives hitherto required to remove the interfering gas. Because of this, the present invention makes it possible to perform the mercury measurement easily without requiring such stringent measurement conditions as hitherto required. Yet, since no inflammable gas is generated from the sample S during the mercury measurement, the amount of the sample S to be measured can be increased as compared with that hitherto employed and, therefore, the total mercury contained in the sample S can be accurately measured.

Figure 2:
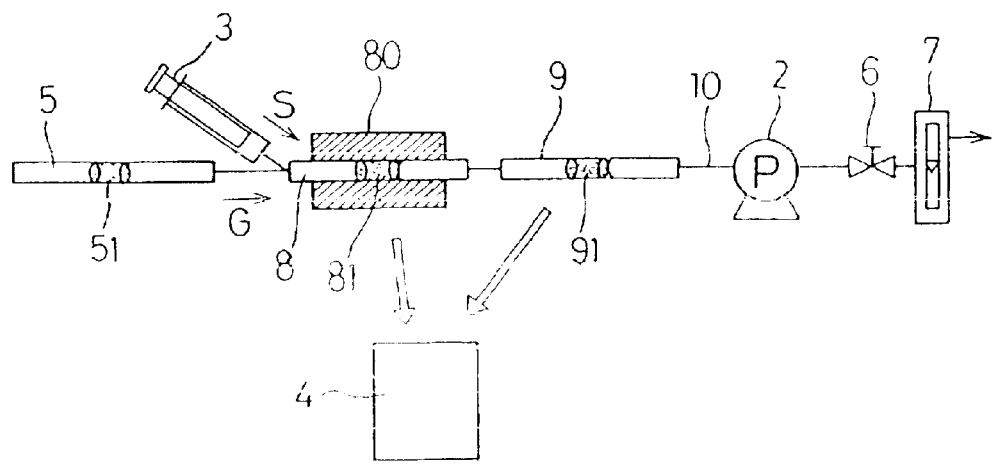
FIG. 2 similarly illustrates a fluid circuit employed in a mercury measuring apparatus according to a second preferred embodiment of the present invention.

FIG. 2 illustrates a schematic configuration of the mercury measuring apparatus according to a second preferred embodiment of the present invention. The measuring apparatus shown therein includes a first column 8 filled with a first adsorbent material 81 effective to adsorb organic mercury, a heater 80 for heating the first column 8 to vaporize metallic mercury contained in the sample S so that the resultant gaseous mercury can flow through the first adsorbent material 81 within the first column 8 while the organic mercury contained in the sample S can be adsorbed by the adsorbent material 81. A second column 9 fluid connected in series with the first column 8 and filled with a second adsorbent material 91 effective to adsorb the metallic mercury.

As is the case with the previously described first embodiment, the suction pump 2 for introducing the air G as a carrier gas is positioned downstream of the first and second column 8 and 9, and the first column 8 is provided with the injector 3 such as a micro-syringe for injecting the sample S into the first column 81 while the carrier air G is flowing through the first column 8. The measuring apparatus shown in FIG. 2 also includes a mercury measuring instrument 4 such as, for example, a heated vapor analyzing device for measuring the organic mercury and the metallic mercury which have been differentiatedly collected by the adsorbent materials 81 and 91 within the first and second columns 8 and 9, respectively. The mercury removal filter 5 is positioned upstream of the first column 8 for removing mercury contained in the carrier air G that is subsequently feed through the first and second columns 8 and 9, and the control valve 6 and the flow meter 7 are fluid-connected with the downstream side of the suction pump 2. Thus, from the upstream side to the downstream side of the system, the mercury removal filter 5, the first and second columns 8 and 9, the suction pump 2, the control valve 6 and the flow meter 7 are connected in series with each other by means of a tubing 10 in the order specified above.

The first adsorbent material 81 filled in the first column 8 is of a kind having a different carrying capacity with respect to metallic mercury and organic mercury (a mercury compound) and, also, hydrocarbon depending on a temperature condition and, for example, activated alumina ($Al_2O_3$) can be suitably employed therefor. This activated alumina exhibits an excellent capability of adsorbing organic mercury even when heated to about 150° C. However, metallic mercury and hydrocarbon when heated to about 150° C. are vaporized to form a gas and will not therefore be adsorbed by the activated alumina. Accordingly, the use of the activated alumina for the first adsorbent material 81 within the first column 8 is effective to differentiate and collect the organic mercury and the metallic mercury.

The second adsorbent material 91 filled in the second column 9 is suitably employed in the form of material effective to form amalgam in reaction with mercury such as a mass of particulates or fine woolen fibers of gold or silver, or material prepared by coating porous carrier with the material, such as gold or silver, effective to form amalgam, as is the case with the filler material 51 in the mercury removal filter 5. The use of any of those materials for the second adsorbent material 91 is effective to ensure adsorption of metallic mercury that has been transformed into a gas by the heater 80.

A method of measuring the mercury according to the second embodiment of the present invention will now be described.

Assuming that the suction pump 2 is being driven, the carrier gas, that is, the air G is fed through the mercury removal filter 5 into the first column 8 and then into the second column 9. As the carrier air G flow through the mercury removal filter 5, mercury contained in the air G is removed by adsorption achieved by the filter material 51 and the mercury-free air G is subsequently supplied towards the first column 8 and then the second column 9.

While the air G flows through the first column 8 in the manner described above, the sample S is injected into the interior of the first column 8. Since at this time the first column 8 is heated by the heater 80, only organic mercury contained in the sample S is adsorbed by the first adsorbent material 81 within the first column 8 and, on the other hand, metallic mercury contained in the sample S is transformed into the gas which flows outwardly from the first column 8 together with hydrocarbon contained in the sample S, without being adsorbed by the first adsorbent material 81. The gaseous metallic mercury having not been adsorbed by the first adsorbent material 81 subsequently flow into the second column 9 together with the hydrocarbon and, therefore, the metallic mercury is then adsorbed and collected by the second adsorbent material 91 within the second column 9.

The hydrocarbon from which the organic mercury and the metallic mercury have been removed by the first and second adsorbent materials 81 and 91 in the manner described above is discharged out of the second column 9 by the suction pump 2 and are thus removed from the first and second columns 8 and 9. Thereafter, the first and second column 8 and 9 are removed from the tubing 10 and are then placed separately in the mercury measuring instruments 4, such as a heated vapor analyzing device, so that measurement can be carried out by thermally vaporizing the organic mercury and the metallic mercury that have been differentiatedly collected by the first and second adsorbent materials 81 and 91 within the first and second columns 8 and 9, respectively.

In this mercury measuring instrument 4, even when the organic mercury and the metallic mercury adsorbed respectively by the first and second adsorbent materials 81 and 91 are vaporized by heating, the hydrocarbon contained in the sample S has already been removed from the first and second columns 8 and 9 and, therefore, no inflammable gas is generated. Also, since only the mercury-free carrier air G and the organic and metallic mercury adsorbed by the adsorbent material 81, 91 are present within the first and second columns 8 and 9 and no interfering gas such as hydrocarbon which would otherwise interfere with measurement of the mercury is present within the first and second columns 8 and 9, there is no need to use any additives hitherto required to remove the interfering gas. Because of this, the present invention makes it possible to easily perform the organic mercury and the metallic mercury measurements separately without requiring such stringent measurement conditions as hitherto required. Yet, since no inflammable gas is generated from the sample S during the mercury measurement, the amount of the sample S to be measured can be increased as compared with that hitherto employed and, therefore, the organic and metallic mercury contained in the sample S can be accurately measured.

According to the second embodiment of the present invention, as hereinabove discussed, it is possible to achieve an accurate measurement by differentiating the organic mercury and the metallic mercury. In contrast thereto, the first mentioned embodiment of the present invention is effective to allow the mercury measuring instrument 4 to measure the total mercury.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. By way of example, the mercury measuring apparatus according to any one of the first and second embodiments of the present invention can be used not only for measuring a liquefied hydrocarbon such as naphtha, but also for measuring a gaseous hydrocarbon.

Accordingly, such changes and modifications are, unless they depart from the scope of the present invention as delivered from the claims annexed hereto, to be construed as included therein.

What is claimed is:

1. A method of measuring the amount of mercury contained in a hydrocarbon, which comprises the steps of:
   causing a gas containing no mercury to flow through a column filled with an adsorbent material effective to adsorb mercury;
   injecting hydrocarbon to be measured into the column while the gas flows through the column to allow the adsorbent material to adsorb mercury contained in the hydrocarbon;
   removing a volatile component other than the mercury together with the mercury-free gas from the column; and
   measuring the mercury by means of a mercury measuring instrument.

2. A method of measuring organic mercury and metallic mercury contained in a hydrocarbon by differentiatedly collecting the organic mercury and the metallic mercury, which method comprises the steps of:
   preparing a first column, filled with a first adsorbent material effective to adsorb organic mercury, and a second column filled with a second adsorbent material effective to adsorb metallic mercury, said first and second columns being fluid-connected in series with each other;
   injecting hydrocarbon to be measured into the first column while a gas containing no mercury is allowed to flow through the first and second columns sequentially;
   heating the first column to transform the metallic mercury contained in the hydrocarbon into a gaseous fluid which flows through the first adsorbent material into the second column and also causes the organic mercury to be adsorbed by the first adsorbent material;
   causing the second adsorbent material within the second column to adsorb the metallic mercury; and
   measuring the organic mercury and the metallic mercury, which have been differentiatedly collected by the first and second columns, respectively, by means of a mercury measuring instrument.

3. The mercury measuring method as claimed in claim 1, wherein the gas containing no mercury is air.

4. The mercury measuring method as claimed in claim 2, wherein the gas containing no mercury is air.

5. An apparatus for measuring mercury contained in a hydrocarbon, which apparatus comprises:
   a column filled with an adsorbent material effective to adsorb mercury;
   a pump for flowing through the column a gas containing no mercury;
   an injector for injecting a hydrocarbon to be measured into the column while the gas flows through the column; and
   a mercury measuring instrument for measuring the mercury which has been adsorbed by the adsorbent material.

6. An apparatus for measuring organic mercury and metallic mercury contained in hydrocarbon by differentiatedly collecting the organic mercury and the metallic mercury, which apparatus comprises:
- a first column, filled with a first adsorbent material effective to adsorb organic mercury;
- a heater for heating the first column so as to allow a gaseous metallic mercury, contained in the hydrocarbon, to flow through the first adsorbent material;
- a second column connected in series with the first column and filled with a second adsorbent material effective to adsorb the metallic mercury;
- a pump for conveying a gas containing no mercury through the first and second columns sequentially;
- an injector for injecting the hydrocarbon to be measured into the first column while the gas containing no mercury flows therethrough; and
- a mercury measuring instrument for measuring the organic mercury and the metallic mercury which have been differentiatedly collected by the first and second columns, respectively.

7. The mercury measuring apparatus as claimed in claim 5, wherein the injector is a micro-syringe.

8. The mercury measuring apparatus as claimed in claim 6, wherein the injector is a micro-syringe.

9. The mercury measuring apparatus as claimed in claim 5, wherein the gas containing no mercury is air, and the pump is disposed downstream of the column with respect to a direction of flow, and further comprising a mercury removal filter disposed upstream of the column for removing mercury from the air to achieve a mercury-free flow through the column.

10. The mercury measuring apparatus as claimed in claim 6, wherein the gas containing no mercury is air, and the pump is disposed downstream of the column with respect to a direction of flow, and further comprising a mercury removal filter disposed upstream of the column for removing mercury from the air to achieve a mercury-free flow through the column.

* * * * *